United States Patent [19]

Pollermann

[11] 4,027,167
[45] May 31, 1977

[54] DIAPHRAGM ARRANGEMENT FOR ADJUSTABLE APERTURE, ESPECIALLY FOR ERECTING A RADIATION BEAM

[75] Inventor: Max Pollermann, Julich, Germany

[73] Assignee: Kernforschungsanlage Julich Gesellschaft mit beschrankter Haftung, Julich, Germany

[22] Filed: June 27, 1975

[21] Appl. No.: 590,792

[30] Foreign Application Priority Data

June 28, 1974 Germany .......................... 2431115

[52] U.S. Cl. ............................. 250/513; 250/512
[51] Int. Cl.² .................................... G21F 5/04
[58] Field of Search ........... 250/505, 511, 512, 513

[56] References Cited
UNITED STATES PATENTS

| 2,542,196 | 2/1951 | Haupt | 250/513 |
| 2,836,729 | 5/1958 | Snarr et al. | 250/512 |
| 3,115,580 | 12/1963 | Brewer | 250/511 |
| 3,156,824 | 11/1964 | Peyser | 250/511 |

*Primary Examiner*—Alfred E. Smith
*Assistant Examiner*—B. C. Anderson
*Attorney, Agent, or Firm*—Walter Becker

[57] ABSTRACT

An adjustable diaphragm arrangement, or device, for defining an aperture which confines a beam of radiation, especially for radiation therapy, in which cup shaped diaphragm elements, the edges of which define the edge of the aperture and which elements are concave toward a common point at or near the source of radiation, are tiltably mounted for simultaneous movement to control the size of the aperture, and may, in addition, be rotatable to vary the orientation of the aperture, all of the aforesaid movements being carried out without change in the axis of the beam of radiation. The parts of the device may be formed of a material which strongly absorbs radiation.

18 Claims, 15 Drawing Figures

DIAPHRAGM ARRANGEMENT FOR ADJUSTABLE APERTURE, ESPECIALLY FOR ERECTING A RADIATION BEAM

The present invention relates to a radiation aperture with a continuously variable opening, in which at least two aperture elements are pivotally connected to a housing or a supporting structure, said aperture elements being arranged perpendicularly with respect to the direction of a bundle of rays confined by an exit opening provided in a mantle of radiation shielding material, which mantle surrounds a source of rays. The aperture elements are arranged in a plurality of superimposed planes and designed in the manner of laminae or are located in one surface and designed as jaws. The aperture elements located within or outside said mantle are so dimensioned that they completely cover the exit opening in said mantle when the aperture is closed.

Radiation apertures of the above mentioned type are employed when employing energy-rich radiation, especially in the radiation therapy, while the radiation by means of the radiation aperture provided between the source of rays and the object to be subjected to radiation is limited to a bundle of rays and is adapted to the object to be subjected to radiation.

Radiation apertures in which aperture elements are provided in the manner of laminae or are arranged as jaws pertain to the state of the art. Thus, British Pat. Nos. 1,029,859 and 1.029,860 describe a radiation aperture in which four aperture parts are crossed in pairs in the manner of double slot apertures and are guided on arc slides. The drawback of this design consists in that a rather complicated guiding and driving system is required. A further disadvantage consists in that due to the arrangement of the aperture elements in different planes, the aperture has about twice the thickness of the aperture elements. In addition thereto, the two pairs are arranged in different planes and further the collimation of the radiation in two directions perpendicular to each other differs from each other.

A radiation aperture with aperture elements likewise guided in the manner of double slot apertures has likewise become known. While this known radiation aperture, for collimating the radiation two collimator systems are arranged one behind the other, the aperture elements are respectively moved along a circular arc with the point of curvature being located in the vicinity of the source of rays. This radiation aperture has the drawback that the movement of the aperture elements is effected by means of a complicated mechanical system.

There has furthermore become known a radiation aperture with aperture elements in the manner of a double slot aperture, according to which for collimating the radiation, the aperture elements are arranged in a plurality of planes one above each other and offset relative to each other. However, also with this known radiation aperture it is disadvantageous that for purposes of obtaining a common movement of the aperture parts, a rather complicated mechanical transfer system is required.

A further radiation aperture has become known according to which the aperture elements consist of four jaws arranged in one plane, which jaws are movably arranged for movement about centers of gravity located in the vicinity of the source of rays. This brings about that the space for the source of rays is greatly limited and confined. While with this known radiation aperture, for purposes of obtaining a collimated scattering of the rays, the inner surfaces of the jaws are directed to the source of rays, it is a great drawback that also in this instance complicated guiding devices are required for carrying out the complicated movements which the four jaws have to execute. The number of devices is furthermore increased due to the fact that for covering gaps which occur at the end faces of the jaws, wedge-shaped intermediate members are provided.

It is, therefore, an object of the present invention to provide a radiation aperture with continuously variable opening with aperture elements designed in the manner of laminae or as jaws, in which the aperture elements are guided and movable in a rather simple manner while the aperture opening is adaptable as to shape and size to the object to be exposed to radiation.

These and other objects and advantages of the invention will appear more clearly from the following specification in connection with the accompanying drawings, in which:

FIG. 1c is a section taken along the line Ic—Ic of FIG. 1a.

FIG. 3a represents a section through the radiation aperture according to the invention with the aperture elements designed in the manner of double angle apertures and perpendicular to the direction of the radiation and extending through the point of intersection of the axes.

FIG. 3b is a top view of the embodiment of the aperture parts of the radiation aperture according to FIG. 3a.

FIG. 4b is a section through the radiation aperture according to FIG. 4a, said section being taken along the line IVb — IVb of FIG. 4a.

FIG. 4d is a top section of a special embodiment of the aperture elements pertaining to the radiation aperture of FIG. 4a, to FIG. 4c; FIG. 4d with the aperture in closed condition.

The radiation aperture according to the present invention is characterized primarily in that the aperture elements are designed as cutouts of ball cup or socket or approximately as cutouts of ball cups or sockets with a common ball point center located in the source of the rays or in the vicinity of the source of the rays, said aperture elements being respectively located in one or two bearings connected to the housing or the supporting construction and pivotal about one or more axes intersecting each other in the common center point of the ball. This arrangement advantageously brings about that not only the movement of the aperture elements for opening and closing the aperture but also complicated movements serving for varying the shape and size of the aperture opening can be carried out as simple pivotal movement. Technically complicated and expensive prisms and arc slide guiding means become superfluous. Rather simple and thus inexpensive ball bearings or wire ball bearings can be employed for journalling the aperture elements. Inasmuch as the ball cup-shaped aperture elements with each movement remain in the ball cup corresponding to their radius about the common center point of the ball, no friction occurs between the aperture elements. Friction occurring during the movement of the aperture elements remains limited to the bearing friction.

An advantageous embodiment of the radiation aperture according to the invention consists in that when providing two bearings for one aperture element, both bearings are arranged on different sides of the point of intersection of the axes at equal distance from the point of intersection of the axes. Due to the fact that the bearings are equally far spaced from the center of gravity of the radiation aperture, they are uniformly stressed or under uniform load. At the same time, the point of intersection of the axes remains free. In this connection, it has proved expedient to arrange the source of rays precisely at the point of intersection of the axes because in this way, the bundle of rays precisely at the point of intersection of the axes because in this way, the bundle of rays is complicated by the aperture elements and thus is sharply scattered.

If the aperture elements of the radiation aperture according to the invention are designed as laminae, the particular design of the aperture elements as ball cups will permit in a further very advantageous embodiment of the radiation aperture according to the invention designing the aperture elements as multi-laminae engaging each other. This brings about an increased shielding of the radiation and at the same time an even better collimation of the bundle of rays will be realized.

When the aperture elements are designed in the manner of double slot apertures with the slots arranged at a right angle to each other, an expedient embodiment of the radiation aperture according to the invention consists in that the aperture elements are arranged for pivoting about two axes one being at a right angle to the other, while each two oppositely located aperture elements are pivotable about a common axis.

A further advantageous embodiment of the radiation aperture according to the invention is seen in the fact that for forming the aperture opening there are provided two aperture elements which are equipped with a square-shaped recess and are pivotal about a common axis. With this design of the radiation aperture according to the invention, the aperture elements are pulled away from each other for purposes of closing the aperture, whereas they are moved toward each other for opening said aperture. A further advantageous development of this design consists in that at least one aperture element is designed as semi-ball cup and is journalled in a wire ball bearing or the like for rotation about an axis which is perpendicular to the common axis of the aperture elements and at the same time forms the normal onto the center point of the recess of the aperture element which is rotatably journalled. In this way, it is also possible to adjust aperture openings which are provided with an opening different from a square or rectangular shape, whereby the bundle of rays is particularly well adaptable to the object to be exposed to radiation.

The principle employed with this embodiment of the radiation aperture according to the invention, namely, to adjust the variable aperture opening with two aperture elements with a square recess for scattering, is also without difficulties applicable to a plane aperture system. The aperture opening will then be adjusted by displacing the plane aperture elements in a direction opposite to each other and to turn said plane aperture elements about the normal on the center point of the recess of the respective aperture element.

A simplification of the drive of the aperture elements is, with the embodiments having a common axis for the aperture elements, obtainable when with a pivotal arrangement of two aperture elements about a common axis, two adjacent bearings which are fixedly connected to the housing or the support construction on the common axis are designed as bevel gears and through a third bevel gear are coupled to each other as bevel gear triple. In this way, the aperture elements which are rotatable about a common axis are movable together and, more specifically, in opposite direction with regard to each other.

If with the embodiment of the radiation aperture according to the invention with rotatable arrangement of two aperture elements with a square recess, aperture openings having a square-shaped or rectangular shape are to be adjusted, it is possible to turn both aperture elements by means of one drive. This is made possible when, with rotatable arrangement of both aperture elements, both aperture elements are designed as semi-ball-shaped cups, and for turning the two aperture elements there are provided two flexible shafts which at their one end are through a gear transmission which is fixedly connected to the housing or the supporting construction and is adapted to the diameter of the aperture elements are connected to each other and to a knurled wheel serving as driving wheel, while at their other ends flexible shafts comprising worms are provided while the worms respectively engage a gear ring connected to an aperture element.

With a further very advantageous embodiment of the device according to the invention, there are provided two aperture elements which form a double angle aperture and respectively have a rectangular recess for the aperture opening and are respectively journalled in a cardanic mounting comprising two rings while said aperture elements are pivotable about two axes arranged at a right angle with regard to each other and while said aperture elements are fixedly connected with the pivotable ring of the respective cardanic mounting, which ring is pivotable about two axes arranged at a right angle with regard to each other. The two cardanic mountings are connected to the housing or the supporting construction and are coaxially arranged with regard to each other in such a way that the axes of the two cardanic mountings, which axes extend at a right angle with regard to each other, coincide in one of the two aperture elements. Due to the fact that the aperture elements are respectively cardanically journalled for pivoting about two axes which are at a right angle with regard to each other, size and lateral ratio of the aperture opening are adjustable by simple pivotal movements of the aperture elements.

A very advantageous embodiment of the radiation aperture according to the invention furthermore consists in that four ball cup-shaped aperture elements forming a jaw aperture are provided. Those confining surfaces of the aperture elements which with the aperture closed are located adjacent to each other, form partial surfaces of two planes which extend perpendicularly with regard to each other and the line of intersection of which is located in the central axis of the bundle of rays. Each two aperture elements arranged adjacent to each other are located in pairs opposite to the other pair of apertures and are respectively pivotally journalled in a cardanic mounting comprising two rings while being pivotable about two axes arranged perpendicular to each other. The two cardanic mountings are connected with the housing or the supporting construction and are coaxially arranged with regard to each other in such a way that the axes of the two cardanic mountings, which axes are perpendicular to each other, will with the aperture closed be arranged in the planes which are perpendicular to each other. The arrangement is such that one aperture element of one pair of apertures is diagonally oppositely located to another aperture element of another pair of apertures. Each of said two aperture elements is fixedly connected to the ring of the respective cardanic mounting, which ring is pivotable about two axes arranged perpendicularly with regard to each other. The respective other aperture element of the two pairs of apertures is connected to a yoke which is pivotable about the axis located in the plane separating the two pairs of apertures from each other when the aperture is closed, said yoke being arranged on a ring of the respective cardanic mounting which is pivotable about two axes arranged perpendicular to each other. The arrangement is such that the aperture element which is connected to the pivotally arranged yoke will, under the influence of a pressure exerting force for instance a spring or the like, be pressed against the respective confining surface of that aperture element which in pivotal direction is located oppositely and is connected to the ring that is pivotable about two axes located perpendicularly to each other.

Due to the fact that both aperture elements of a pair of apertures are connected to the ring pivotable about two axes arranged perpendicularly with regard to each other, while one of said two aperture elements is not fixedly connected to the ring but is pivotably connected through a yoke that is pivotable about an axis common to both aperture elements, a relative movement of the two aperture elements with regard to each other will be made possible and, more specifically, in the pivotal direction of said yoke. This relative movement consists in that the aperture element, which is pivotally arranged through the intervention of said yoke, is displaced relative to that aperture element of the same pair of apertures which is fixedly connected to the ring that is pivotable about two axes arranged perpendicularly with regard to each other. This last mentioned aperture element is, due to the influence of a pressure exerting force, pressed against that aperture element of the other pair of apertures which in pivotal direction is located opposite and is fixedly connected with the ring of the other cardanic mounting which is pivotable about two axes arranged perpendicularly with regard to each other. If now the two aperture elements which are fixedly connected in the respective cardanic mounting with the rings pivotable about two axes arranged perpendicularly with regard to each other are spaced from each other, the two other aperture elements are automatically displaced in the direction toward the aperture elements which respectively are located opposite to each other in the pivotal direction of their yokes so that an aperture opening is formed which is confined by all four aperture elements.

Expediently, designs of the radiation aperture according to the invention with cardanically journalled aperture elements consist in the ring of the outer cardanic mounting, which ring is pivotable about two axes arranged perpendicularly with regard to each other, is designed as the outer ring of the outer cardanic mounting and that the ring of the inner cardanic mounting, which ring is pivotable about two axes which are perpendicular to each other, is designed as inner ring of the inner cardanic mounting. Furthermore, for purposes of simultaneous pivoting in counter directions of the aperture elements about a common axis, one bearing each of the adjacent supporting rings of the two cardanic mountings is designed as bevel gear while the mountings designed as bevel gears are coupled to each other through a third bevel gear as bevel gear triple or triplex. Said last mentioned aperture elements are fixedly connected with the rings that are pivotable about two axes arranged perpendicularly with regard to each other. Furthermore, for purposes of pivoting the two aperture elements which are fixedly connected to the rings pivotable about two axes located at a right angle to each other, there are provided two flexible shafts which at one end are connected to a knurled wheel or the like which serves as driving wheel and is connected to the housing or the supporting construction, while the other ends of said flexible shafts are respectively provided with worms.

If the two above mentioned designs of the radiation aperture according to the invention with cardanically mounted aperture elements are combined with each other, the cardanically mounted aperture elements are pivotable in opposite direction with regard to each other about axes which are arranged at a right angle with regard to each other. As a result thereof, the aperture opening will with all sizes and side conditions of the aperture opening remain centered about the central axis of the bundle of rays. The design of the radiation aperture according to the invention, in which four aperture elements are provided in the form of jaws as parts of a ball cup, is characterized in that the thickness of the closure equals the screening thickness. This design is in particular with penetrating rays or when the space is rather limited, applicable in an advantageous manner. At the same time, due to the design of the aperture elements, it will be assured that the bundle of rays of a source of rays arranged in the point of intersection of the axes is collimated by the aperture elements in each adjusted position of the aperture. Inasmuch as during the opening of the aperture each time the displacement of the aperture element (which is pivotable by a yoke) relative to the fixedly connected aperture element of the respective pair of apertures is effected by pivoting about an axis common to both aperture elements of the pair of apertures, no gap disadvantageous for the screening occurs between the two aperture elements of the aperture pair. Furthermore, the angles of the aperture opening, which angle is formed by the aperture elements of a pair of apertures, will always amount to 90°. This, however, does not apply to the other angles of the aperture opening which amount to more than 90° in view of the spherical excesses depending on the size of the aperture opening. Therefore, when opening the aperture a wedge-shaped gap occurs between the two confining surfaces (pressed against each other) of the aperture elements connected to the pivotally arranged yokes and the aperture elements respectively located oppositely in the pivoting direction. As a result thereof, the respective wedge angle $\epsilon$ equals half the spherical excess of the spherical rectangle or square which forms the aperture opening. According to a formula of the spherical geometry, $$\epsilon = \frac{I \times 180°}{2r^2 \times \pi},$$

in which $I$ represents the contents of the surface of the aperture opening and r represents the radius of the ball.

While with an opening angle of the aperture elements of 30° the wedge-shaped gap amounts to only about 3 percent of the aperture opening, the wedge-shaped gap is nevertheless expediently screened by the fact that the confining surfaces of the aperture elements which face each other and are pressed against each other have ball-shaped ribs and recesses designed around the point of intersection of the axes while said ribs respectively engage oppositely located recesses. The said screening may also be effected by the fact that the two aperture elements which are connected to the respective pivotally arranged yokes, have screening strips overlapping confining surfaces which due to a pressure force are pressed against aperture elements which in pressing direction are located oppositely. The gap occurring when the aperture opening is covered by the ribs or the screening strips which are taken along without interfering with the aperture opening. In this connection, it has proved expedient that the ribs or the screening strips, for increasing the screening effect, are made of highly absorbing material, for instance tungsten or enriched uranium.

As experience has proved, the size of the gap which is disadvantageous for the screening can be reduced by slanting the confining surfaces which face toward the aperture elements connected to the pivotally arranged yokes and which belong to the aperture elements which in pivotal direction are located oppositely and are fixedly connected with the rings which are pivotable about two axes arranged at a right angle with regard to each other. This slanting starts from a line which is adjacent to the partial surfaces which with the closed aperture are covered by the pressed-on surfaces of the aperture elements covered with pivotally arranged yokes. The slanting amounts to half the spherical excess of the full aperture opening freed by moving away from each other the ball-shaped aperture elements. This slanting is such that the aperture elements which are connected to the pivotally arranged yokes engage the aperture elements located oppositely in pivoting direction and do so with closed as well as fully opened aperture opening without the formation of gaps. The slanting is thus always outside the partial surfaces of the aperture elements fixedly connected to the pivotally arranged yokes, which partial surfaces are covered when the aperture is closed. If the slanting is so arranged that it comprises only the opened partial surfaces of the fixedly connected aperture elements which partial surfaces are covered with fully opened aperture, an intermediate range remains which is expediently rounded. This brings about that the gap occurring in intermediate positions of the aperture is less than would correspond to the spherical excess. If additionally the confining surfaces of the aperture elements which are pressed against each other, are provided with ribs and rib-receiving recesses or screening strips, the gap will be fully covered.

Figure 1A:
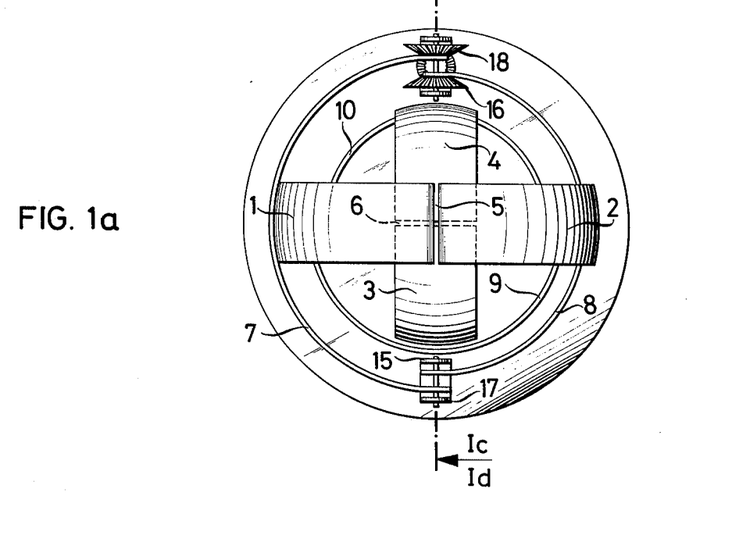
FIG. 1a is a top view of an embodiment of a radiation aperture according to the invention with aperture elements designed in the manner of double slot apertures.
Figure 1B:
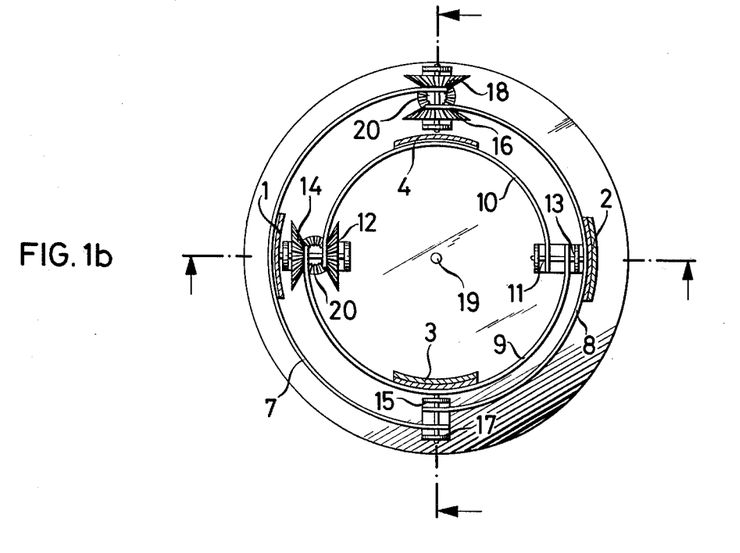
FIG. 1b is a section through the radiation aperture according to FIG. 1a, said section being taken in a direction perpendicular to the direction of the radiation and through the point of intersection of the axes.
Figure 1C:
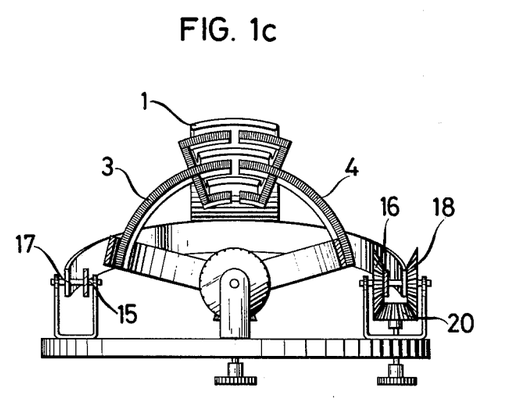
Figure 1D:
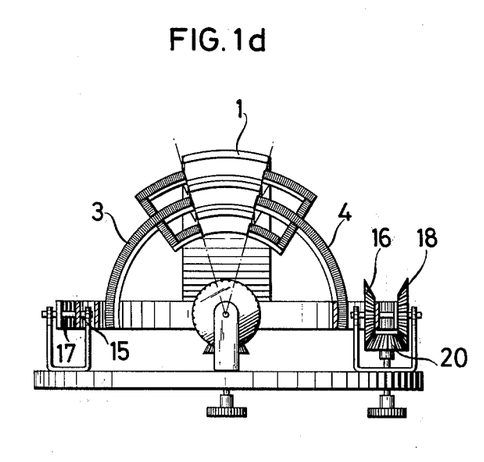
FIG. 1d represents a section through the aperture of FIG. 1a along the line Id—Id.
Figure 1E:
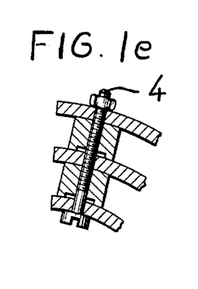
FIG. 1e is a fragmentary view showing how the laminae of an aperture element can be interconnected.

Referring now to the drawings in detail, it will be seen from FIG. 1a in connection with FIGS. 1c and 1d, that the aperture elements 1–4 are designed in the manner of a double slot aperture with slots 5, 6 which are arranged perpendicularly with regard to each other and form parts of ball cups. These aperture elements 1–4 are, as will be seen from FIG. 1b, by means of yokes 7–10 journalled in pairs for pivoting about a common axis for each pair. The bearings 11 and 12, 13 and 14, 15 and 16 as well as 17 and 18 are in equally spaced arrangement from the intersection of the axes located along axes which are perpendicular to each other, in such a way that the point 19 of intersection of the axes remains free. The bearing pairs 12 and 14 and 16 and 18 respectively located on a common axis are designed as bevel gears and through a third bevel gear 20 are interconnected in the form of a bevel gear triplex so that the particular elements 1 and 2 as well as 3 and 4 are respectively movable together in opposite directions by moving the bevel gears 20. As a result thereof, the slots 5 and 6 are opened or closed. For instance, the aperture elements 3 and 4 which in FIGS. 1c and 1d are designed as multiple laminae occupy the position shown in the drawing. FIG. 1e shows how bolt means 4' can be employed to connect the laminae of an aperture element together.

Figure 2A:
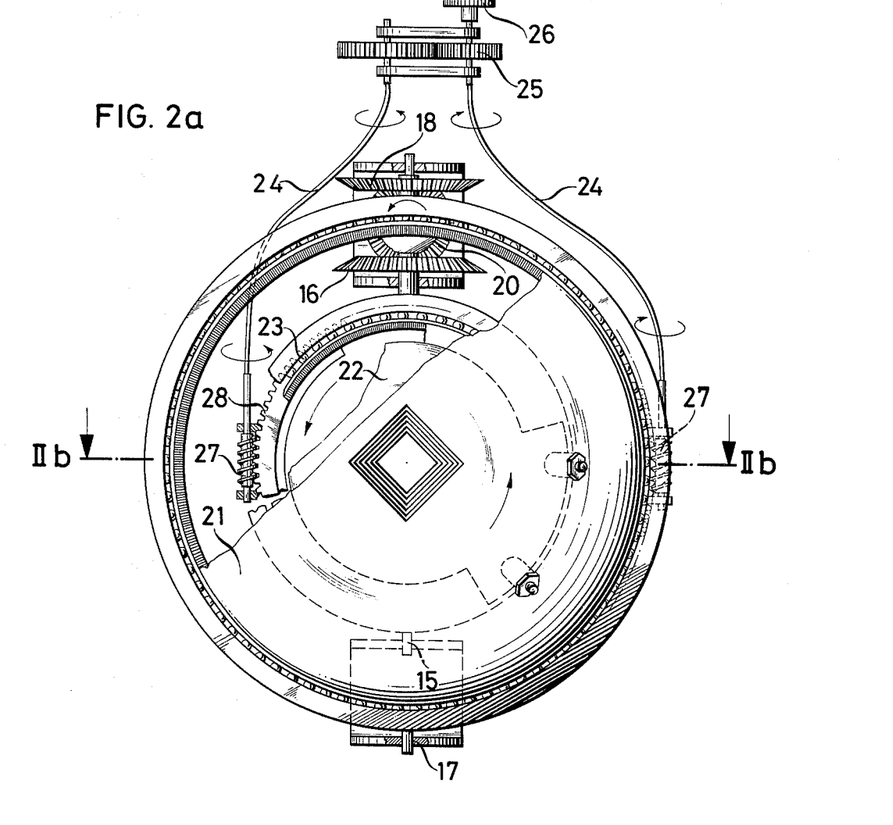
FIG. 2a is a partial top view of an embodiment of the radiation aperture according to the invention in the manner of an apertured partition in combination with a partial section through the radiation aperture in a direction perpendicular to the radiation and through the point of intersection of the axes.
Figure 2B:
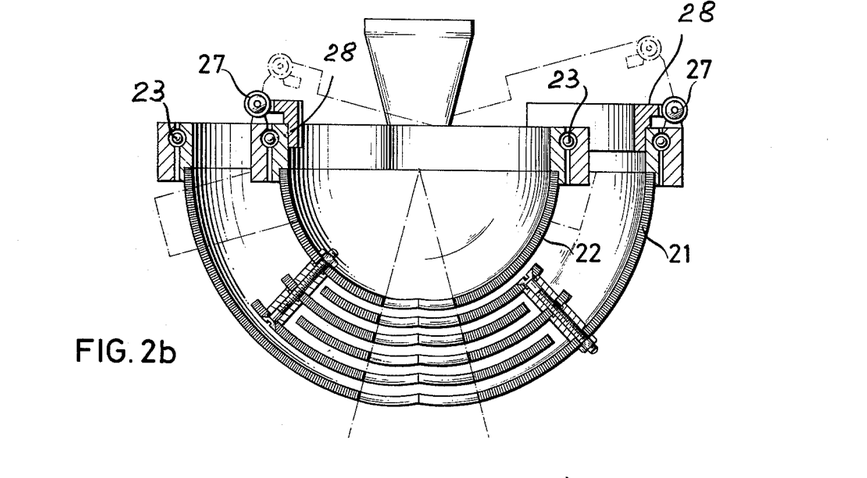
FIG. 2b illustrates a section through the radiation aperture of FIG. 2a, said section being taken along the line IIb—IIb of FIG. 2a with the aperture occupying its open position.

The embodiment of the radiation aperture according to the invention as illustrated in FIGS. 2a and 2b has two aperture elements 21 and 22 with a square-shaped recess which, as will be seen from the drawing and the particular FIG. 2b are designed as ball semi-cups and at the same time as multilaminae. The aperture elements 21, 22 are, as shown in FIG. 2a, illustrated partially for the aperture element 22 and are each journalled in a respective ring 28 by means of a wire ball bearing 23. The two aperture elements are pivotally mounted in the bearings 15 and 16 and 17 and 18 for pivoting about a common axis. The bearings 16 and 18 are designed as bevel gears and are supplemented to form a triplex by a third bevel gear 20 serving as driving wheel. For purposes of turning the two aperture elements 21 and 22 each about one axis which is perpendicular on the common axis of the two aperture elements and forms the normal onto the center point of the respective recess, there are provided flexible shafts 24. These shafts 24 are at one end thereof connected to each other and to a knurled wheel 26 serving as driving wheel by means of a gear transmission 25 adapted to the diameter of the aperture elements. At their other ends, said shafts 24 are provided with worms 27 which respectively mesh with a gear ring 28 connected to an aperture element; in FIG. 2a merely the gear ring of the aperture element 22 is partially shown. This arrangement brings about that both aperture elements can be turned in the same direction by the same angle whereby rectangular aperture openings, not shown in the drawing, can be adjusted at any desired side ratio. By individually driving the two aperture elements, it is possible to set non-illustrated forms of the aperture opening which are different from the rectangular form of the aperture.

Figures 3A, 3B:
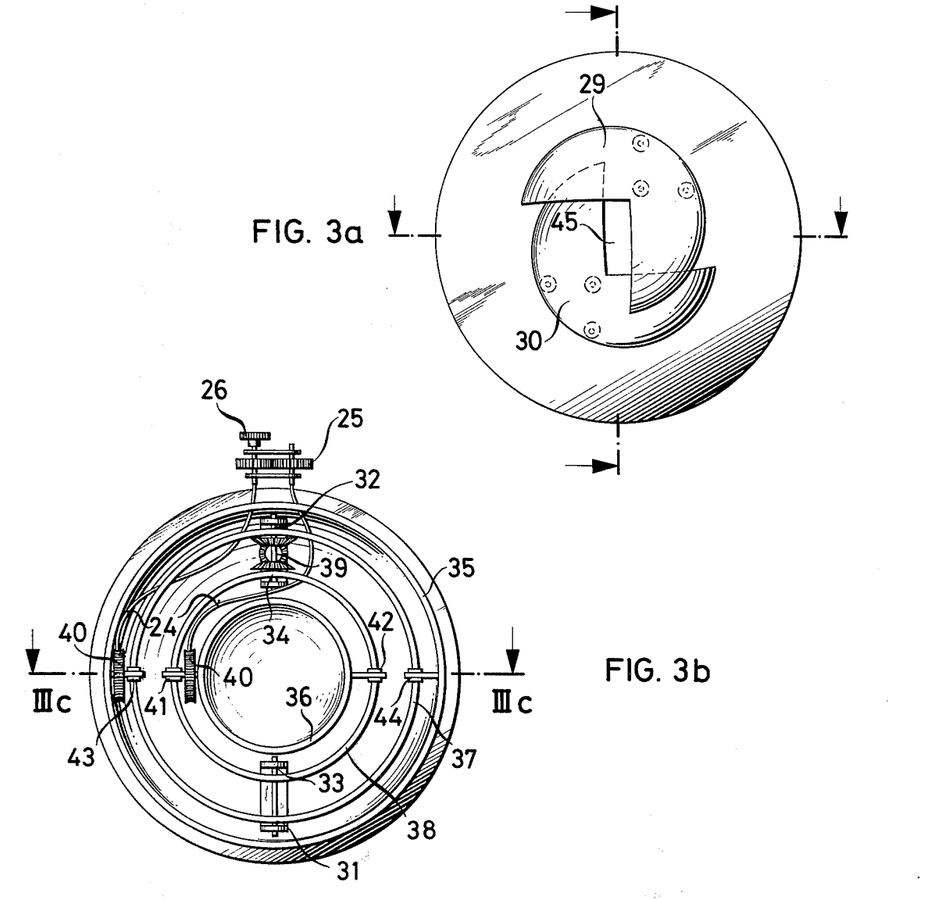
Figure 3C:
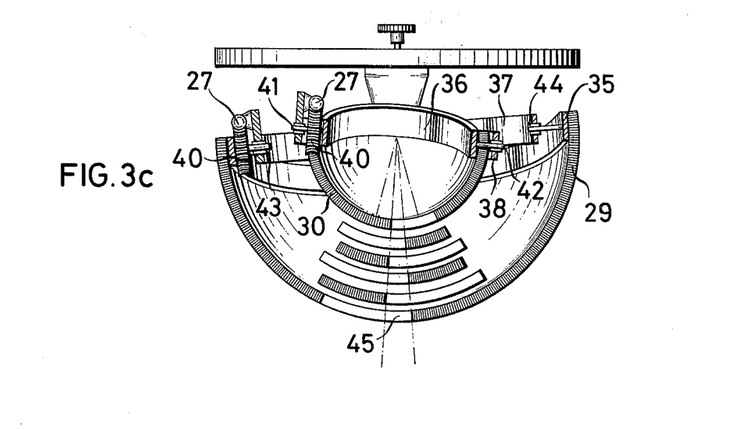
FIG. 3c represents a section through the radiation aperture according to FIGS. 3a and 3b, said section being taken along the line IIIc — IIIc of FIG. 3b.

The embodiment in FIGS. 3a–3c of the radiation aperture according to the invention has two aperture elements, 29, 30 which form a double angle aperture with rectangular recess for the aperture opening. These aperture elements 29, 30, as will be seen from FIG. 3c, are designed as ball semi-cups and at the same time form multi-laminae. Each of the two aperture elements 29, 30 is pivotally journalled in the bearings 31 and 32 as well as bearings 33 and 34 in a cardanic mounting having two rings. The outer aperture part 29 is, as will be seen from FIG. 3d and FIG. 3c, fixedly connected to the outer ring 35 of the outer cardanic mounting which outer ring 35 is pivotal about two axes arranged at a right angle with regard to each other. The inner aperture element 30 is fixedly connected to the inner ring 36 of the inner cardanic mounting which inner ring 36 is likewise pivotal about two axes arranged perpendicular with regard to each other. The supporting rings 37 and 38, which are arranged adjacent to each other and respectively pertain to the two cardanic mountings, are interconnected by means of a bevel gear triplex 39 and are pivotable in opposite directions about one of the two axes of the two cardanic mountings, which axes are arranged at a right angle with regard to each other. For purposes of simultaneous opposite pivoting of the two aperture elements 29 and 30 about the other common axis of the two aperture elements, there are provided two flexible shafts 24 which at one end thereof are interconnected through two equal sized intermeshing gears 25 and are interconnected and connected to a knurled wheel 26 serving as driving wheel while having their other ends provided with worms 27 which mesh with worm wheels 40 interconnecting rings 35 and 36. Through the intervention of the flexible shafts, the rings 35 and 36 to which the aperture elements 29 and 30 are fixedly connected are pivotable in the bearings 41 and 42 as well as in the bearings 43 and 44. The illustration of FIG. 3c shows a position of the aperture elements 29 and 30 which corresponds to the diaphragm opening or aperture opening 45 in FIG. 3b.

Figure 4A:
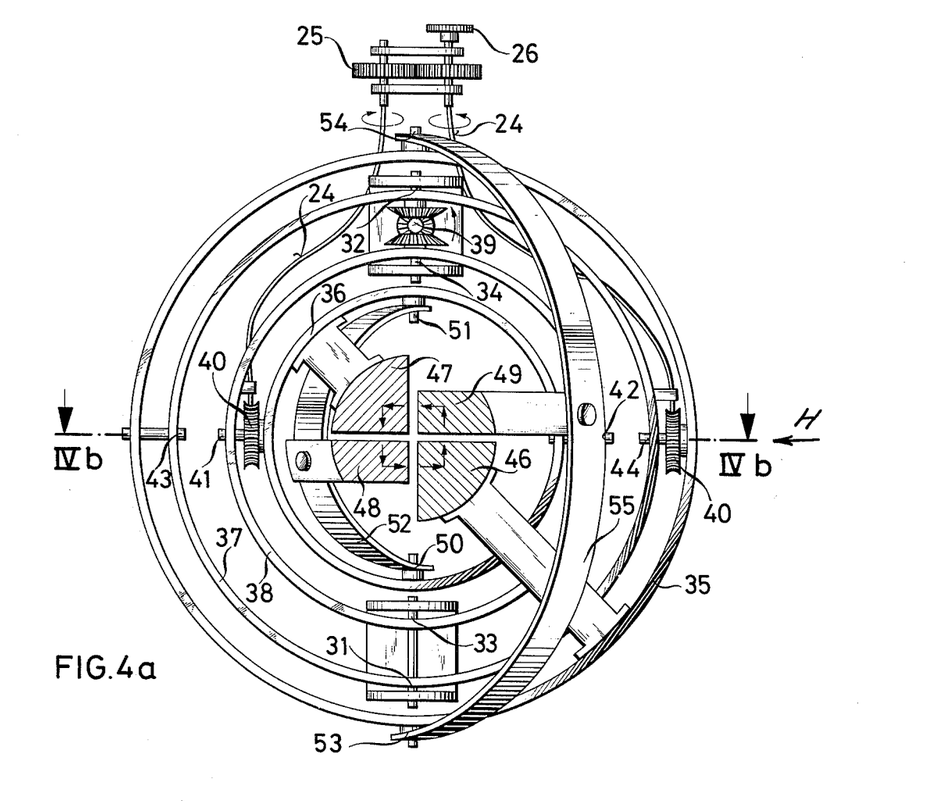
FIG. 4a is a top view of a radiation aperture according to the invention with the aperture elements designed as jaws.
Figure 4B:
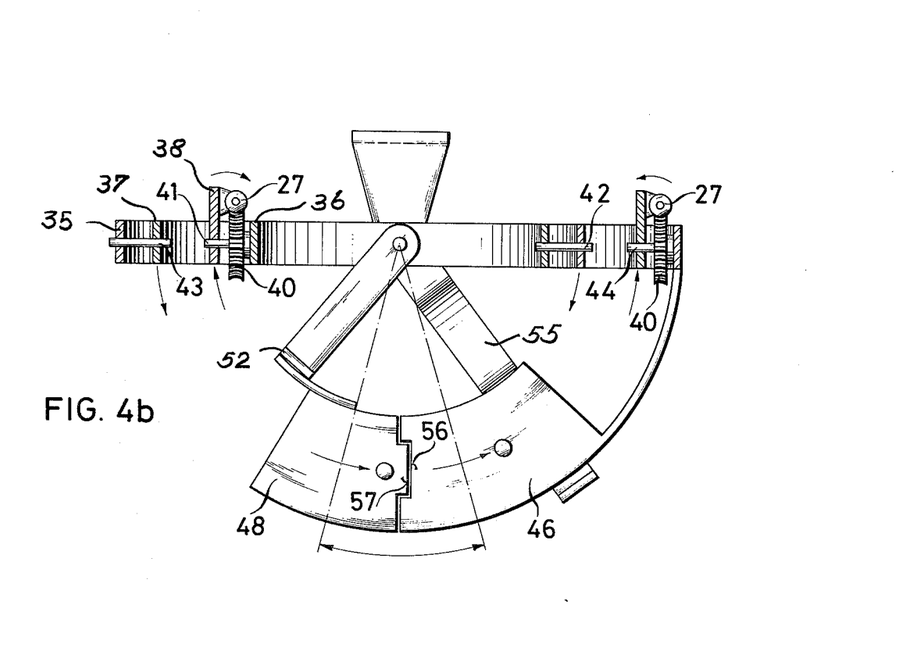

The embodiment of the radiation aperture according to the invention as illustrated in FIGS. 4a–4e has four aperture elements 46–49 which have the shape of jaws and form parts of a ball cup and which in FIG. 4a for reason of a better view of the cardanic mounting are illustrated on a reduced scale and which as shown in FIG. 4b at 46 and 48 are designed as parts or ball cups. The confining surfaces, as will be seen from FIGS. 4a and 4b, form partial surfaces of two planes which are arranged perpendicularly with regard to each other and the line of intersection of which is located in the central axis of the bundle of rays. Two adjacent aperture elements each 46 and 49 as well as 47 and 48 form a pair of apertures which are respectively connected with a cardanic mounting. The two cardanic mountings are journalled in bearings 31 and 32 and 33 and 34. They are coaxially arranged with regard to each other in such a way that the axes of the cardanic mountings are arranged perpendicularly with regard to each other and located according to FIG. 4a with closed aperture into the planes which are perpendicularly arranged with regard to each other. Both aperture elements 46 and 49 as well as 47 and 48 of a pair of apertures are connected to the respective rings 35 and 36 which are pivotable about two axes arranged at a right angle with regard to each other. The aperture element 48 is connected to the yoke 42 pivotably journalled in the bearings 50 and 51, whereas the aperture element 49 is connected to the yoke 55 which is pivotally arranged in the bearings 53 and 54.

For driving the aperture elements 46 and 47, the bevel gear triplex 39 is provided as well as the flexible shaft 24. The triplex 39 interconnects the supporting rings 37 and 38 of the two cardanic mountings. The flexible shafts 24 have one end thereof interconnected by means of two intermeshing gears 25 of identical size and have furthermore connected thereto a knurled wheel 26. At their other ends, said shafts 24 are provided with worms 27 which mesh with worm gears 40 connected to the rings 35 and 36. The rings 35 and 36 by means of which the aperture elements are interconnected are through the shafts 24 pivotable in bearings 41 and 42 as well as the bearings 43 and 44. In this way, and by means of the bevel gear triplex 39, it is possible to adjust the aperture elements 46 and 47 in the direction of the arrows illustrated in FIG. 4a. The aperture elements 48 and 49, which have their confining surfaces respectively located opposite the aperture elements 46 and 47 when viewing the pivoting direction, are pressed against the aperture elements 46 and 47 and are likewise movable in the direction of the arrows shown in FIG. 4a while the aperture elements 48 and 49 follow the direction of the arrows pointing in the direction toward the respective oppositely located aperture elements 46 and 47 in view of a spring force not shown acting thereupon.

As will be seen from FIG. 4b at 46 and 48, the confining surfaces of the aperture elements, which surfaces face toward each other, are provided with a recess 56 and with a rib 57 engaging said recess.

Figure 4C:
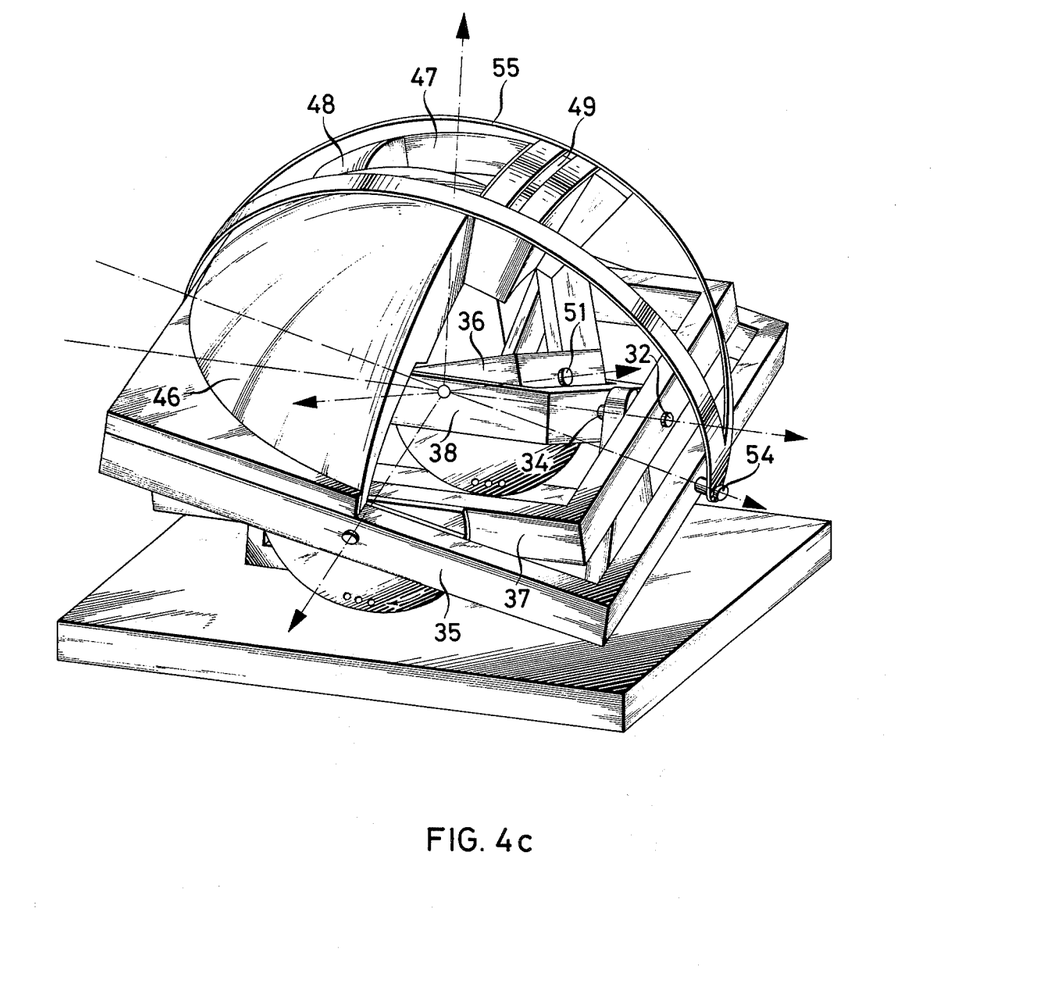
FIG. 4c represents an isometric view of a model of an embodiment of the radiation aperture according to FIGS. 4a and 4b when viewing FIG. 4a in the direction of the arrow H.

FIG. 4c shows a model of the radiation apertures illustrated in FIGS. 4a and 4b with the aperture in open condition.

Figure 4D:
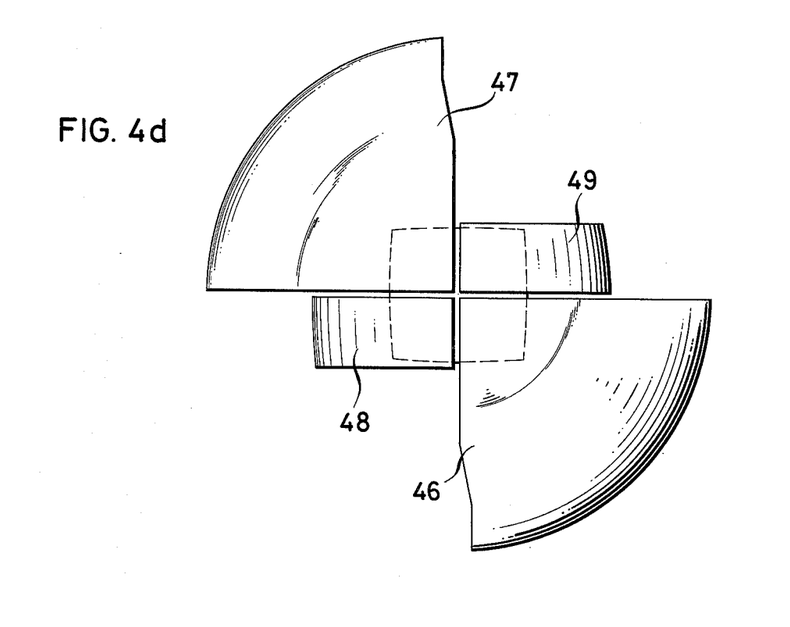
Figure 4E:
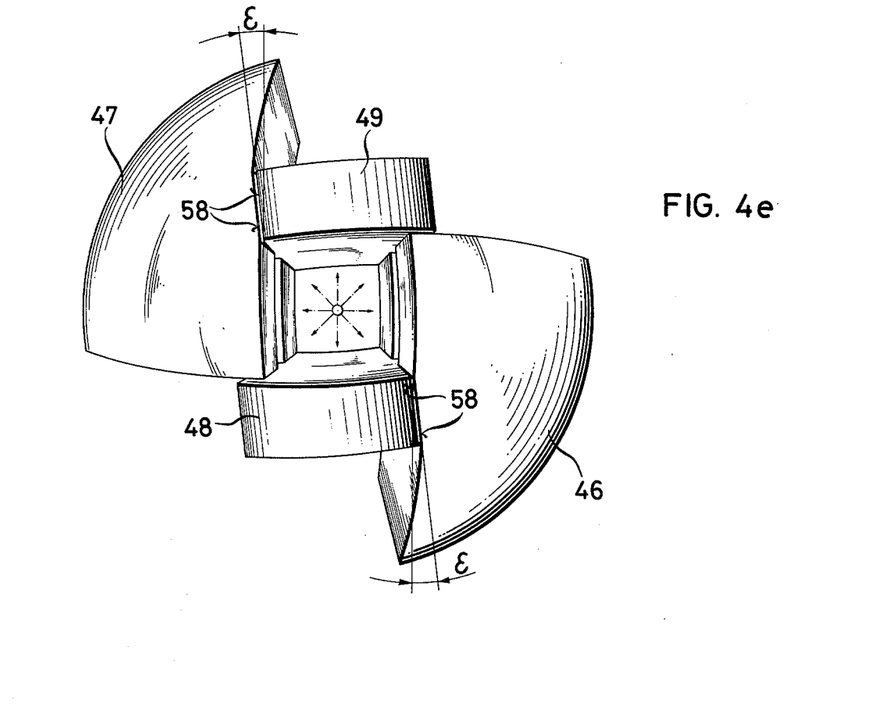
FIG. 4e shows the same view as FIG. 4d but with the aperture in open condition.

In FIGS. 4d and 4e, the aperture elements 46 and 47 as well as 48 and 49 are illustrated with closed and opened aperture. It will be seen from FIG. 4d that in the closed condition all parts are arranged closely adjacent to each other. Inasmuch as the aperture elements or diaphragm elements 46 and 47 are slanted, it will be appreciated from FIG. 4e that also with fully opened aperture no gap appears between the partial surfaces 58 engaging each other and pertaining to confining surfaces of the aperture elements, which surfaces face each other. When the slanting of the aperture elements 46 and 47 is lacking, it will be clear from FIG. 4e and the illustrated angle $\epsilon$ that with fully opened aperture a gap would occur with an opening angle $\epsilon$.

It is, of course, to be understood that the present invention is, by no means, limited to the specific showing in the drawings but also comprises any modifications within the scope of the appended claims.

What is claimed is:

1. In an adjustable radiation diaphragm device; a support, spherical shell diaphragm elements movably mounted on the support and defining a variable aperture for defining a beam of radiation emanating from a source stationary relative to said support, said spherical shell diaphragm elements being in the form of ball sections concave toward a common mid point near the source of radiation, and journalling means supporting said spherical shell diaphragm elements for pivotal movement about axis means passing through said common mid point in order to form continuously variable diaphragm opening adjustable in size thereby.

2. An adjustable radiation diaphragm device according to claim 1 in which said axis means comprises a pair of axes intersecting at said common point.

3. An adjustable radiation diaphragm device according to claim 1 which includes a pair of bearings on opposite sides of said common point supporting each diaphragm element and defining a pivot axis therefor.

4. An adjustable radiation diaphragm device according to claim 1 in which each diaphragm element comprises multiple laminae with the laminas of one diaphragm element interfitting with those of at least one other diaphragm element.

5. In an adjustable radiation diaphragm device; a support diaphragm elements movably mounted on the support and defining a variable aperture for defining a beam of radiation emanating from a source stationary relative to said support, said diaphragm elements being in the form of ball sections concave toward a common point near the source of radiation, and means supporting said diaphragm elements for pivotal movement about axis means passing through said common point, said diaphragm elements comprising a set of four with a pair in opposed relation in each of two perpendicular planes having a line of intersection passing through said common point, the diaphragm elements of each pair thereof being pivotal in respectively opposite directions about a respective axis in the plane of the other pair thereof and passing through said common point.

6. An adjustable radiation diaphragm device according to claim 5 in which said diaphragm elements are concentric and each has a square aperture therein, said axis means comprising a common axis passing through said common point and about which said diaphragm elements are both pivotal.

7. An adjustable radiation diaphragm device according to claim 6 in which each diaphragm element is hemispherical with the aperture in about the middle thereof, a bearing ring in the plane of said common point supporting each diaphragm element, each bearing ring being tiltably supported on said common axis, and each diaphragm element being rotatable on the respective bearing ring.

8. An adjustable radiation diaphragm device according to claim 5 which includes gearing interconnecting said diaphragm elements for effecting equal movement thereof in respectively opposite directions for variation of the aperture size without change of the axis thereof.

9. An adjustable radiation diaphragm device according to claim 6 which includes means engaging said bearing rings and operable for rotating said bearing rings equal amounts in the same direction simultaneously.

10. In an adjustable radiation diaphragm device; a support, diaphragm elements movably mounted on the support and defining a variable aperture for defining a beam of radiation emanating from a source stationary relative to said support, said diaphragm elements being in the form of ball sections concave toward a common point near the source of radiation, and means supporting said diaphragm elements for pivotal movement about axis means passing through said common point, said diaphragm elements comprising a pair of concentrically arranged cups each having a notch formed into the periphery with the notches diametrically opposed so the edges of the notches define the edges of the aperture, a first ring on which each diaphragm element is mounted and pivotal about a first axis extending through said common point, a second ring on which each first ring is pivotal about a second axis perpendicular to said first axis and also passing through said common point, the said axes for one of said diaphragm elements being coaxial with the axes for the other of the diaphragm elements in one position of the diaphragm elements.

11. In an adjustable radiation diaphragm device; a support, diaphragm elements movably mounted on the support and defining a variable aperture for defining a beam of radiation emanating from a source stationary relative to said support, said diaphragm elements being in the form of ball sections concave toward a common point near the source of radiation, and means supporting said diaphragm elements for pivotal movement about axis means passing through said common point, said diaphragm elements comprising four cup shaped elements having opposed edges with two sets of opposed edges in planes substantially perpendicular to one another, said planes intersecting in a line passing through said common point, a first pair of said elements being arranged in diametrically opposed relation, a first ring connected to each of said pair of elements and pivotal about a first axis passing through said common point and in one of said planes of said edges, a second ring on which each first ring is pivoted and pivotal about a second axis perpendicular to said first axis and also passing through said common point, the respective pivot axes for said pair of elements being respectively coaxial in one position of said elements, a further pair of said elements also diametrally opposed and associated with respective ones of said first pair of elements and together therewith forming said sets of edges, each further element being pivotally mounted on the said first ring pertaining to the respective first element for tilting movement thereon about an axis perpendicular to the respective first axis and in the plane of said second axes.

12. An adjustable radiation diaphragm device according to claim 11 in which the second axes of said rings are coaxial and said rings are concentric with one another in one position of said elements, and gearing interconnecting said second rings for simultaneous tilting movement thereof in respective directions about said second axis.

13. An adjustable radiation diaphragm device according to claim 11 which includes drive means engaging said first rings and operable for simultaneously tilting said first rings on the said first axes thereof.

14. An adjustable radiation diaphragm device according to claim 11 in which said drive means comprises worm wheels connected to said first rings, worms engaging said worm wheels, and means for simultaneously rotating said worms to tilt said rings in respective directions on said first axes thereof.

15. An adjustable radiation diaphragm device according to claim 11 in which the elements forming a said set of opposed edges have interengageable rib and recess means formed on the edges.

16. An adjustable radiation diaphragm device according to claim 11 in which said further pair of elements comprise screening strips spring pressed against the respective one of said first pair of elements.

17. An adjustable radiation diaphragm device according to claim 16 in which at least said screening strips are formed of a material which is highly effective for radiation absorption.

18. An adjustable radiation diaphragm device according to claim 10 in which each of said further pair of elements has an edge slidably engaging an edge of a respective one of said first pair of elements, each said edge of at least said first pair of elements being formed of angularly related sections whereby said further pair of elements remains in firm sliding engagement with the respective ones of said first pair of elements in all adjusted positions of said elements.

* * * * *